US010633711B2

(12) United States Patent
Yan et al.

(10) Patent No.: US 10,633,711 B2
(45) Date of Patent: Apr. 28, 2020

(54) METHODS FOR RAPID AND SENSITIVE DETECTION OF HOTSPOT MUTATIONS

(71) Applicant: Duke University, Durham, NC (US)

(72) Inventors: Hai Yan, Durham, NC (US); Yiping He, Durham, NC (US); Rui Yang, Durham, NC (US); Bill H. Diplas, Durham, NC (US); Landon Hansen, Durham, NC (US); Darell Bigner, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/505,777

(22) PCT Filed: Aug. 24, 2015

(86) PCT No.: PCT/US2015/046519
§ 371 (c)(1),
(2) Date: Feb. 22, 2017

(87) PCT Pub. No.: WO2016/032947
PCT Pub. Date: Mar. 3, 2016

(65) Prior Publication Data
US 2017/0247765 A1 Aug. 31, 2017

Related U.S. Application Data

(60) Provisional application No. 62/041,197, filed on Aug. 25, 2014.

(51) Int. Cl.
C12Q 1/6886 (2018.01)
(52) U.S. Cl.
CPC ..... C12Q 1/6886 (2013.01); C12Q 2600/156 (2013.01); C12Q 2600/158 (2013.01); C12Q 2600/16 (2013.01); C12Q 2600/166 (2013.01)

(58) Field of Classification Search
None
See application file for complete search history.

(56) References Cited

U.S. PATENT DOCUMENTS

| | | | | |
|---|---|---|---|---|
| 2008/0090233 A1* | 4/2008 | Garcia | ................. | C12Q 1/6886 435/6.14 |
| 2009/0081663 A1* | 3/2009 | Paitan | .................... | C12Q 1/689 435/6.15 |
| 2013/0072397 A1* | 3/2013 | Radlwimmer | ... | G01N 33/57407 506/9 |
| 2013/0143747 A1* | 6/2013 | Gutin | .................... | C12Q 1/6886 506/7 |
| 2013/0210001 A1* | 8/2013 | Lee | ...................... | C12Q 1/6818 435/6.11 |

FOREIGN PATENT DOCUMENTS

| | | |
|---|---|---|
| CN | 103571953 A | 2/2014 |
| CN | 103923976 A | 7/2014 |
| JP | 2012501652 A | 1/2012 |
| SG | 11201701220 A | 3/2017 |
| WO | 2010083250 A2 | 7/2010 |
| WO | 2010139010 A1 | 12/2010 |

OTHER PUBLICATIONS

Remke et al. (2013) Acta Neuropathol. 126:917-929 ; DOI 10:1007/s00401-013-1198-2.*
Catteau et al. (2014) ActaNeuropathologica vol. 2:58 http://www.actaneurocomms.org/content/2/1/58 teach IDH1/2.*
Killela et al. TERT promoter mutations occur frequently in gliomas and a subset of tumors derived from cells with low rates of self-renewal. PNAS 110(15): 6021-6026. (Year: 2013).*
Yan et al. IDH1 and IDH2 mutations in gliomas. New England Journal of Medicine 360(8): 765-773. (Year: 2009).*
Latorra et al. Enhanced Alllele-Specific PCR Discrimination in SNP Genotyping Using 3' Locked Nucleic Acid (LNA) Primers. Human Mutation 22:79-85. (Year: 2003).*
GenBank AF128893 [online] May 13, 1999 [retrieved on Apr. 7, 2019] retrieved from: https://www.ncbi.nlm.nih.gov/nuccore/4808972 (Year: 1999).*
GenBank NG_023319 [online] Feb. 27, 2013 [retrieved on Apr. 7, 2019] retrieved from: https://www.ncbi.nlm.nih.gov/nuccore/300244504 (Year: 2013).*
GenBank NG_023302 [online] Jul. 7, 2010 [retrieved on Apr. 7, 2019] retrieved from: https://www.ncbi.nlm.nih.gov/nuccore/300192901?sat=14&satkey=2408883 (Year: 2010).*
Germer et al. Single-Tube Genotyping without Oligonucleotide Probes. Genome Research 9:72-78. (Year: 1999).*
Morandi et al. Allele Specific Locked Nucleic Acid Quantitative PCR (ASLNAqPCR): An Accurate and Cost-Effective Assay to Diagnose and Quantify KRAS and BRAF Mutation. PLoS One, vol. 7, iss 4, e36084 (13 pages). (Year: 2012).*
Japanese Office Action issued in related Japanese Application No. 2017-511219, dated May 16, 2018.
Liu et al., "Highly prevalent TERT promoter mutations in aggressive thyroid cancers," Endocr. Relat. Cancer. 2013; 20(4);603-610.
Written Opinion issued in related Singaporean Application No. 11201701220P, dated Feb. 5, 2018.
Extended European Search Report issued in corresponding European Application No. 15837033.8, dated Jun. 15, 2018.
Labussiere et al., "Combined analysis of TERT, EGFR, and IDH status defines distinct prognostic glioblastoma classes;" Neurology, Aug. 22, 2014, pp. 1200-1206.
Nonoguchi et al., "TERT promoter mutatiosn in primary and secondary glioblastomas," Acta Neuropathologica, vol. 126, No. 6, Dec. 1, 2013, pp. 931-937.

(Continued)

Primary Examiner — Samuel C Woolwine
(74) Attorney, Agent, or Firm — Banner & Witcoff, Ltd.

(57) ABSTRACT

Methods that rapidly, sensitively, and specifically detect mutations in IDH1/2 and the TERT promoter employ amplification of particular portions of the genes that experience frequent and exquisitely localized mutations. The ability to distinguish between sequences that differ only by one nucleotide and which may be present in very low ratios is essential for such an assay.

21 Claims, 11 Drawing Sheets
Specification includes a Sequence Listing.

(56) References Cited

OTHER PUBLICATIONS

Apr. 26, 2018 (SG) Search Report—Application No. 10201805800X.
International Search Report for PCT/US2015/046519 (dated Feb. 1, 2016).
Killela, PJ et al., 'Mutations in IDH1, IDH2, and in the TERT promoter define clinically distinct subgroups of adult malignant gliomas', Oncotarget, Jan. 28, 2014, vol. 5, No. 6, pp. 1515-1525.
Heindenreich, B. et al. Telomerase Reverse Transcriptase Promoter Mutations in Primary Cutaneous Melanoma: *Homo sapiens* Isolate 14 Telomerase Reverse Transcriptase (TERT) Gene, Promoter Region: Genbank: KJ442777.1. Submitted Feb. 10, 2014, p. 1.
Chien, WW et al., 'BEAMing and Droplet Digital PCR Analysis of Mutant IDH1 mRNA in Glioma Patient Serum and Cerebrospinal Fluid Extracellular Vesicles', Molecular Therapy Nucleic Acids, Jul. 23, 2013, vol. 2, e109, pp. 1-10.
Catteau, A., et al. 'A New Sensitive PCR Assay for One-Step Detection of 12 IDH1/2 Mutations in Glioma', Acta Neuropathologica Communications, Jun. 2, 2014, vol. 2, No. 58, pp. 1-12.
Remke, M. et al., 'TERT Promoter Mutations Are Highly Recurrent in SHH Subgroup Medulloblastoma', Acta Neuropathol., 2013, vol. 126, pp. 917-929.
Diplas et al. "Sensitive and rapid detection of TERT promoter and IDH mutations in diffuse gliomas" Neuro-Oncology, 21(4), 440-450, 2019.
Ichimura "TERT promoter mutation as a diagnostic marker for diffuse gliomas" Neuro-Oncology, 21(4), 417-419, 2019.

\* cited by examiner

| Scenario | Specimen | Tumor % | Sequencing result | True result |
|---|---|---|---|---|
| High tumor % | | >90% | Mutation | Mutation |
| Lower tumor % High normal % | | ~30% | WT *False negative* | Mutation |
| High tumor % Low subclonal % | | >90% | 1. Mutation 2. WT *False negative* | 1. Mutation 2. Mutation |

Normal cell  Cancer cell  Mutation

Fig. 4

SEQUENCE LISTING

<160> NUMBER OF SEQ ID NOS: 32

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
ctgggagggc ccggag                                                    16

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
ctgggagggc ccggaa                                                    16

<210> SEQ ID NO 3
<211> LENGTH: 19
<212> TYPE: DNA

```
<213> ORGANISM: Artificial Sequence
<220> FEATURE:
<223> OTHER INFORMATION: Primer

<400> SEQUENCE: 3
gtcctgcccc ttcaccttc                                               19

<210> SEQ ID NO 4
<211> LENGTH: 16
<212> TYPE: DNA
<213> ORGANISM: Artificial Sequence
<220> FEATURE:
<223> OTHER INFORMATION: Primer

<400> SEQUENCE: 4
cccgtcccga cccctc                                                  16

<210> SEQ ID NO 5
<211> LENGTH: 16
<212> TYPE: DNA
<213> ORGANISM: Artificial Sequence
<220> FEATURE:
<223> OTHER INFORMATION: Primer

<400> SEQUENCE: 5
cccgtcccga cccctt                                                  16

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
cagcgctgcc tgaaactc                                                18

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
gggtaaaacc tatcatcata ggtcg                                        25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gggtaaaacc tatcatcata ggtca                                        25

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aacatgcaaa atcacattat tgcc                                         24
```

```
<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
atcccccggc ttgtgagt                                                    18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
aagcccatca ccattggcag                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aagcccatca ccattggcaa                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aggtcagtgg atcccctctc                                                  20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggaccaagcc catcaccatt                                                  20

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gggtaaaacc tatcatcata ggtt                                             24

<210> SEQ ID NO 16
<211> LENGTH: 24
<212> TYPE: DNA
<213> ORGANISM: Artificial Sequence
<220> FEATURE:
```

```
<223> OTHER INFORMATION: Primer

<400> SEQUENCE: 16
gggtaaaacc tatcatcata ggtg                                  24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gggtaaaacc tatcatcata ggta                                  24

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gggtaaaacc tatcatcata ggtct                                 25

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aagcccatca ccattggcat                                       20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
aagcccatca ccattggcg                                        19

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
aagcccatca ccattggct                                        19

<210> SEQ ID NO 22
<211> LENGTH: 9
<212> TYPE: DNA
<213> ORGANISM: Artificial Sequence
<220> FEATURE:
<223> OTHER INFORMATION: Primer

<400> SEQUENCE: 22 cgggtcccc                                                    9
```

```
<210> SEQ ID NO 23
<211> LENGTH: 8
<212> TYPE: DNA
<213> ORGANISM: Artificial Sequence
<220> FEATURE:
<223> OTHER INFORMATION: Primer

<400> SEQUENCE: 23 ggcccagc                                                                    8

<210> SEQ ID NO 24
<211> LENGTH: 9
<212> TYPE: DNA
<213> ORGANISM: Artificial Sequence
<220> FEATURE:
<223> OTHER INFORMATION: Primer

<400> SEQUENCE: 24 atgacttac                                                                   9

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
ttgatcccca taagcatga                                                       19

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tcactcaaag ccgctcaact ac                                                   22

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
tctgccttca tttcgttatg tacc                                                 24

<210> SEQ ID NO 28
<211> LENGTH: 18
<212> TYPE: DNA
<213> ORGANISM: Inovirus enterobacteria phage M13

<400> SEQUENCE: 28
tgtaaaacga cggccagt                                                        18

<210> SEQ ID NO 29
<211> LENGTH: 18
<212> TYPE: DNA
<213> ORGANISM: Inovirus enterobacteria phage M13

<400> SEQUENCE: 29
caggaaacag ctatgacc                                                        18
```

<210> SEQ ID NO 30
<211> LENGTH: 16
<212> TYPE: DNA
<213> ORGANISM: Artificial Sequence
<220> FEATURE:
<223> OTHER INFORMATION: antisense mutant primer

<400> SEQUENCE: 30
tagggagggc ccggaa                                                          16

<210> SEQ ID NO 31
<211> LENGTH: 16
<212> TYPE: DNA
<213> ORGANISM: Homo sapiens

<400> SEQUENCE: 31
ctccctcccg ggcctt                                                          16

<210> SEQ ID NO 32
<211> LENGTH: 16
<212> TYPE: DNA
<213> ORGANISM: Homo sapiens

<400> SEQUENCE: 32
ctccctcccg ggcctc                                                          16
```

METHODS FOR RAPID AND SENSITIVE DETECTION OF HOTSPOT MUTATIONS

TECHNICAL FIELD OF THE INVENTION

This invention is related to the area of genetic and biochemical assays. In particular, it relates to assays of neoplastic samples and their components.

BACKGROUND OF THE INVENTION

Malignant gliomas are the most common primary central nervous system (CNS) malignancy in adults, responsible for >14,000 deaths in the U.S. in 2012[2]. The World Health Organization (WHO) has established a number of histologic and clinical criteria used for classifying gliomas into various subtypes and grading them I to IV, indicating their degree of malignancy. Diffuse gliomas (WHO grade II-IV), which include astrocytomas, oligodendrogliomas, oligoastrocytomas, and glioblastomas (GBM)[3] are of particular clinical importance as they account for 80% of all primary malignant brain tumors. These tumors are diffusely infiltrative, which makes curative surgical resection impossible. Additionally, grade II-III diffuse gliomas also have the ability to progress to higher WHO grade IV GBM. GBM is the most common malignant brain tumor in adults and has the worst survival (median overall survival 12-15 months)[4]. Additionally, even among entities with identical histology, patient outcome can vary substantially. This is best exhibited by primary GBM, which occurs de novo as compared to secondary GBM, which progresses from lower grades. Both tumors histologically are indistinguishable, but genetically and clinically these diseases are distinct, as the survival of patients with secondary GBM is almost double that of primary GBM[5].

Accurate diagnosis of diffuse glioma is particularly challenging due to heterogeneity, invasiveness, reactive parenchyma, and ambiguity among morphologic features. These diagnostic challenges are reflected by the high degree of inter-observer variability seen in clinical use of these criteria. In a study of 244 gliomas reviewed independently by four neuropathologists, concordance rates were as low as 52%[6]. Accurate diagnosis of diffuse glioma is critically important for clinical decision-making for patients. This diagnosis determines the treatment regimen, and particular subtypes are known to show increased treatment response to particular chemotherapies (e.g., procarbazine, CCNU, and vincristine for oligodendroglioma treatment). Additionally, histologic subtype dictates patient prognosis. Objective, tumor specific markers are clearly needed for more accurate diagnosis, prognosis and delivery of personalized care to glioma patients.

To address these needs, large-scale sequencing studies have profiled the genetic alterations found in diffuse glioma. Many alterations were noted, such as frequent mutations in isocitrate dehydrogenase 1 and 2 (IDH1/2)[1], the promoter of telomerase reverse transcriptase (TERT)[7], alpha thalassemia mental retardation syndrome X-linked (ATRX)[8,9], homolog of Drosophila capicua (GIG), far upstream element binding protein 1 (FUBP1)[10], among others. These findings have helped to establish clear objective molecular subtypes of glioma. In terms of relevance to diagnosis, alterations in the TERT promoter and IDH1/2 are the most promising due in large part to their frequency and their occurrence as single nucleotide substitutions at specific genomic loci ("hotspots"). In diffuse glioma, we found that the degree to which these mutations co-occur or occur exclusively defines glioma subtypes: e.g., IDH1/2 mutations occur in >50% of secondary GBMs but are infrequent in primary GBMs (<5%) (FIG. 1), while TERT promoter mutations are found in >80% of primary GBMs as well as in >70% of oligodendrogliomas (FIG. 2). Furthermore, we found that the genetic subtypes of glioma established by TERT/IDH status effectively stratifies glioma patients into subtypes with distinct prognoses, more effectively than by histology alone, providing physicians with an objective test to guide more appropriate treatment (FIG. 3). For example, patients with gliomas harboring TERT promoter mutations have median overall survival (OS) of 11.5 months, while those with both TERT promoter and IDH1/2 mutations exhibit a median OS of 125 months. Additionally, our studies have revealed that the "mixed histology" oligoastrocytomas, which likely reflect the ambiguity of histologic classification most, genetically stratify into either a astrocytic ($TERT^{WT}IDH^{MUT}$) or oligodendroglial ($TERT^{MUT}IDH^{MUT}$) signature (FIG. 3). We have expanded our study of these mutations to a number of other tumor types and found that TERT promoter mutations are also frequent in other cancers, most notably liver cancer (44.2%), bladder cancer (66%), myxoid liposarcoma (79.1%), and medulloblastoma (21%), in which early diagnosis, recurrence and therapeutic response monitoring is critical[7,11]. (FIG. 2) Similarly, IDH1 and IDH2 mutations have been found in high frequencies in other types of cancers as well, including chondrosarcoma (56%)[12], enchondroma (87%), spindle cell hemangioma (70%)[13,14], acute myeloid leukemia (15%)[15], and cholangiocarcinoma of intrahepatic origin (22-28%)[16].

These glioma subtype-specific and highly recurrent mutations call for diagnostic assays that are able to rapidly, sensitively, and specifically detect these mutations in IDH1/2 and the TERT promoter. Such a tool would aid neuropathologists in these challenging diagnoses, provide patients with more precise prognostic information, and allow physicians to tailor therapy to a patient tumor's unique molecular signature. Additionally, for the many other aforementioned cancer types with frequent mutations in IDH1/2 and the TERT promoter at these loci, such a diagnostic tool would assist in rapid and sensitive detection of these mutations also.

Current diagnostic efforts for mutation detection are based on Sanger sequencing, which is time-consuming, costly, and most importantly is limited by poor sensitivity (limit of detection ~20% mutant alleles)[17]. Samples of low tumor percentage (<40% tumor, for heterozygous mutations implies <20% mutant alleles) can be misdiagnosed as lacking mutations due to limited sensitivity (FIG. 4, 5). Such scenarios of low tumor percentage are very realistic in the context of diffuse glioma and other malignancies. In addition to the inherent heterogeneity and invasive nature of diffuse glioma, tumor biopsies can contain minimal tumor tissue, leading to poor sampling. Necrosis is a feature common to many cancers that can also limit usable tissue. These limitations have significant diagnostic and prognostic implications and can result in misguided therapy, making them inadequate for clinical use.

There is a continuing need in the field to make clinical analyses faster, more sensitive, and more specific.

SUMMARY OF THE INVENTION

According to one aspect of the invention a method is provided for testing a body sample of a human with a tumor. Tumor DNA of a body sample of the human is amplified with a set of amplification primers. Each amplification primer comprises a sequence selected from SEQ ID NO:

1-14. Amplification products comprising TERT promoter and IDH1 and IDH2 sequences are thereby generated. Thereafter, the amplification products are detected.

According to another aspect of the invention a heterozygous calibrator plasmid for TERT/IDH1 is provided. The plasmid comprises (a) a TERT C228T segment and a TERT C250T segment, and (b) an IDH1 R132H segment and an IDH1 wild type segment, wherein each of the TERT segments is present in equal amounts and sizes, and wherein each of the IDH1 segments is present in equal amounts and sizes. The plasmid has restriction sites between each segment that enables selective linearization and addition of other loci of interest, such as, but no limited to, other IDH1 and IDH2 mutations, and other genetic loci of interest.

One aspect of the invention comprises a method for detecting mutations in IDH1/2 and/or TERT promoter in a subject comprising, consisting of, or consisting essentially of (a) obtaining a body sample from the subject, the sample comprising at least one tumor DNA; (b) providing at least one nucleic acid primer to the sample; (c) providing enzymes and reagents for amplification of the at least one DNA template using the at least one primer; (d) incubating the sample, enzymes, reagents, at least one primer under conditions suited for amplification of the at least one DNA template; (e) detecting the amplified nucleotides; and (f) identifying mutations in IDH1/2 and/or TERT promoter.

In some embodiments, the at least one primer is selected from the group consisting of those primers found in Table 1A, Table 1B and Table 2, and combinations thereof.

In other embodiments, the enzymes and reagents comprise those found in Table 4.

In yet another embodiment, the sample is incubated under conditions according to Table 3.

In some embodiments, the subject is a mammal. In other embodiments, the subject is a human.

In other embodiments, the biological sample is selected from the group consisting of cerebral spinal fluid (CSF), tissues, cells, biopsies, blood, lymph, serum, plasma, urine, saliva, mucus, and tears. In some embodiments, the sample comprises a tissue biopsy. In some embodiments, the biological sample comprises CSF. In some embodiments, the biological sample comprises urine. In some embodiments the biological sample comprises plasma.

These and other embodiments which will be apparent to those of skill in the art upon reading the specification provide the art with assays which are robust, rapid, and reproducible.

BRIEF DESCRIPTION OF THE DRAWINGS

FIG. 1 was previously published in Yan, H. et al. IDH1 and IDH2 mutations in gliomas. *N Engl J Med* 360, 765-73 (2009).[1]

FIG. 2 was previously published in Killela, P. J. et al. TERT promoter mutations occur frequently in gliomas and a subset of tumors derived from cells with low rates of self-renewal. *Proc Natl Acad Sci USA* 110, 6021-6 (2013).[7]

FIG. 4. Potential issues with sampling tissue from cancer patients. False negatives can result from low percentages of tumor cells in a background of normal tissue or from a subclonal tumor cell population in a background of other cancer cells.

DETAILED DESCRIPTION OF THE INVENTION

Figure 1:
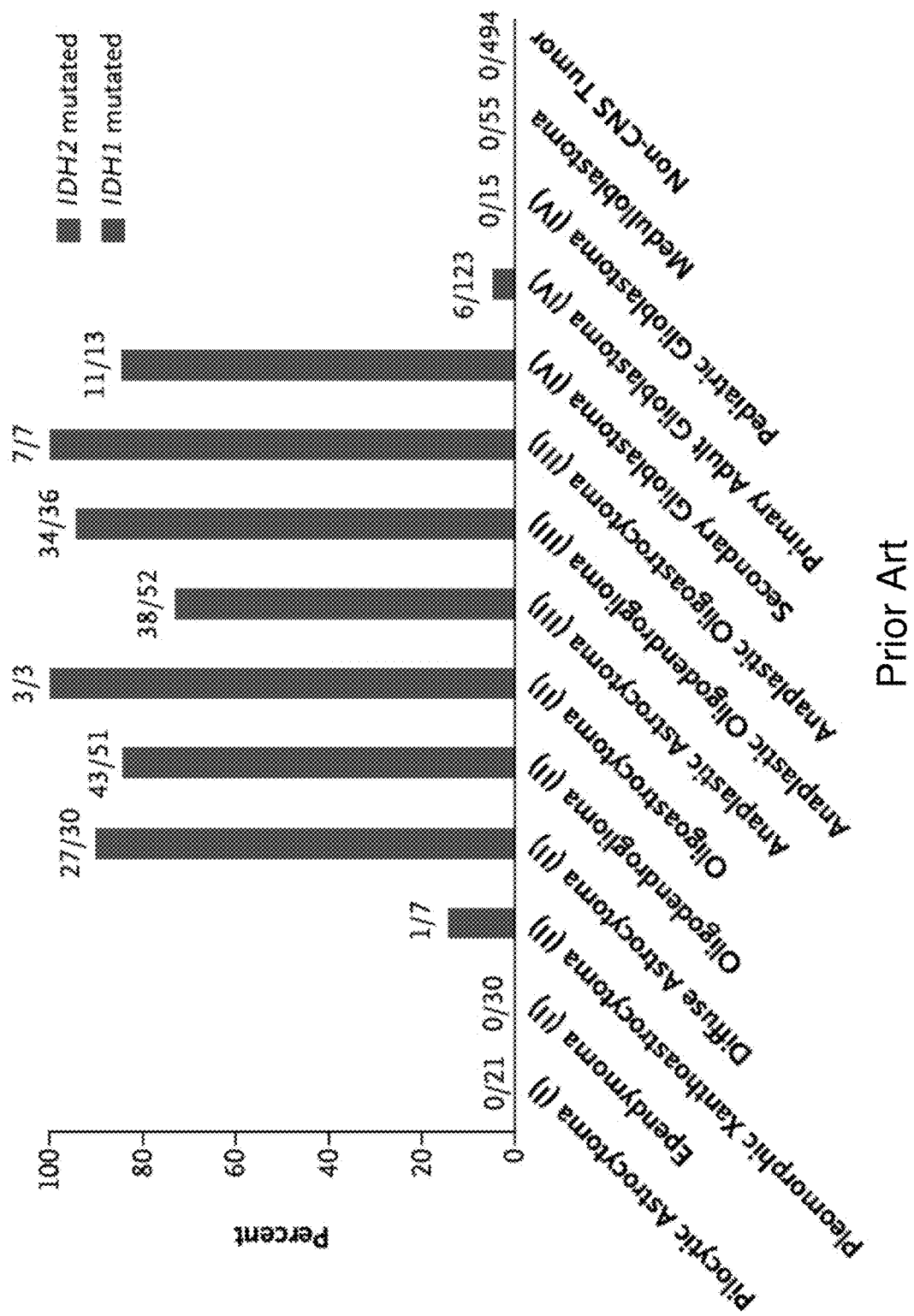
FIG. 1. Mutations in IDH1 and IDH2 across different tumor types. IDH1 and IDH2 mutations occur frequently in diffuse glioma (WHO grade II-III) and secondary GBM (WHO grade IV).
Figure 2:
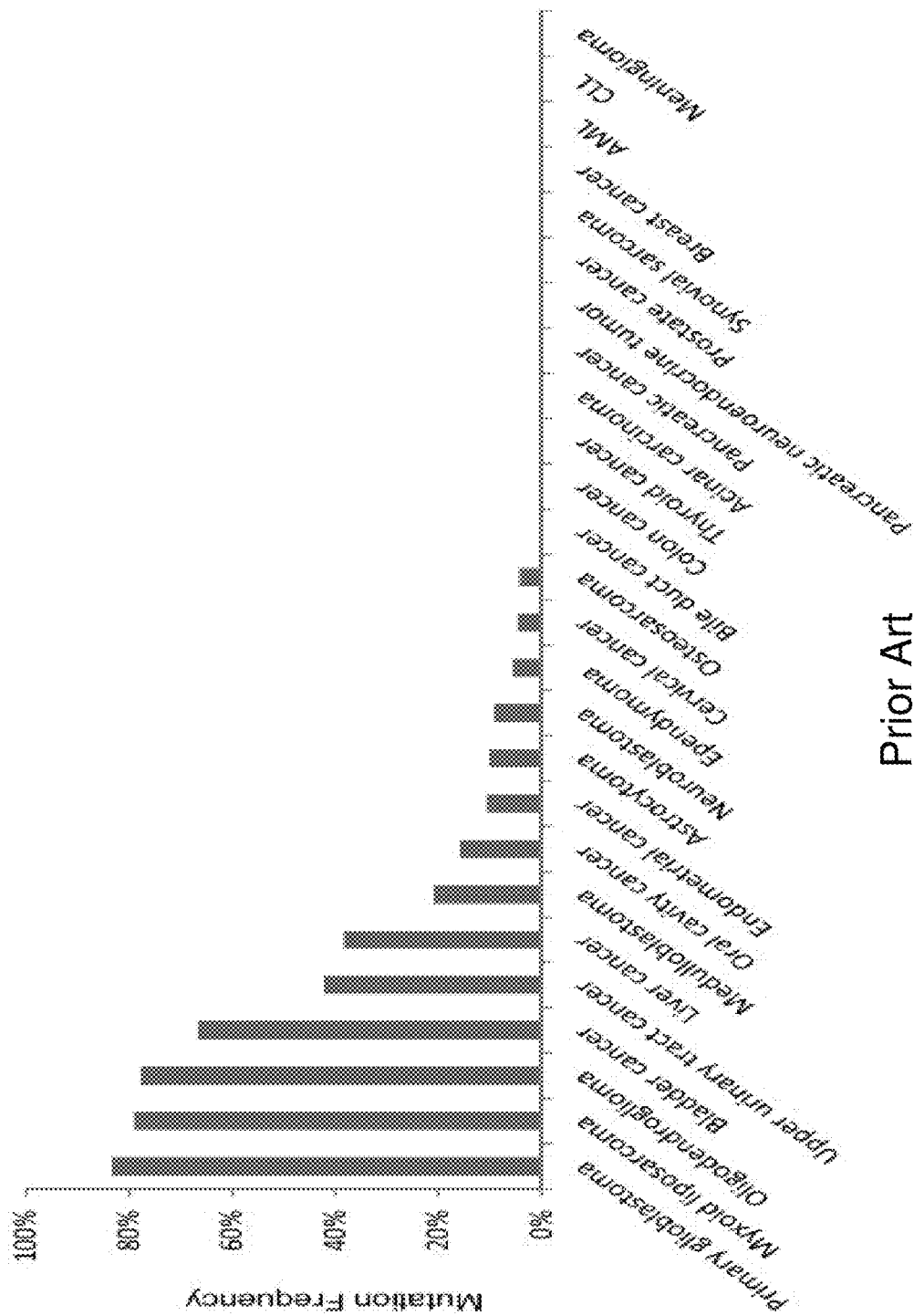
FIG. 2. Frequency of TERT promoter mutations across a large panel of tumor subtypes.
Figure 3:
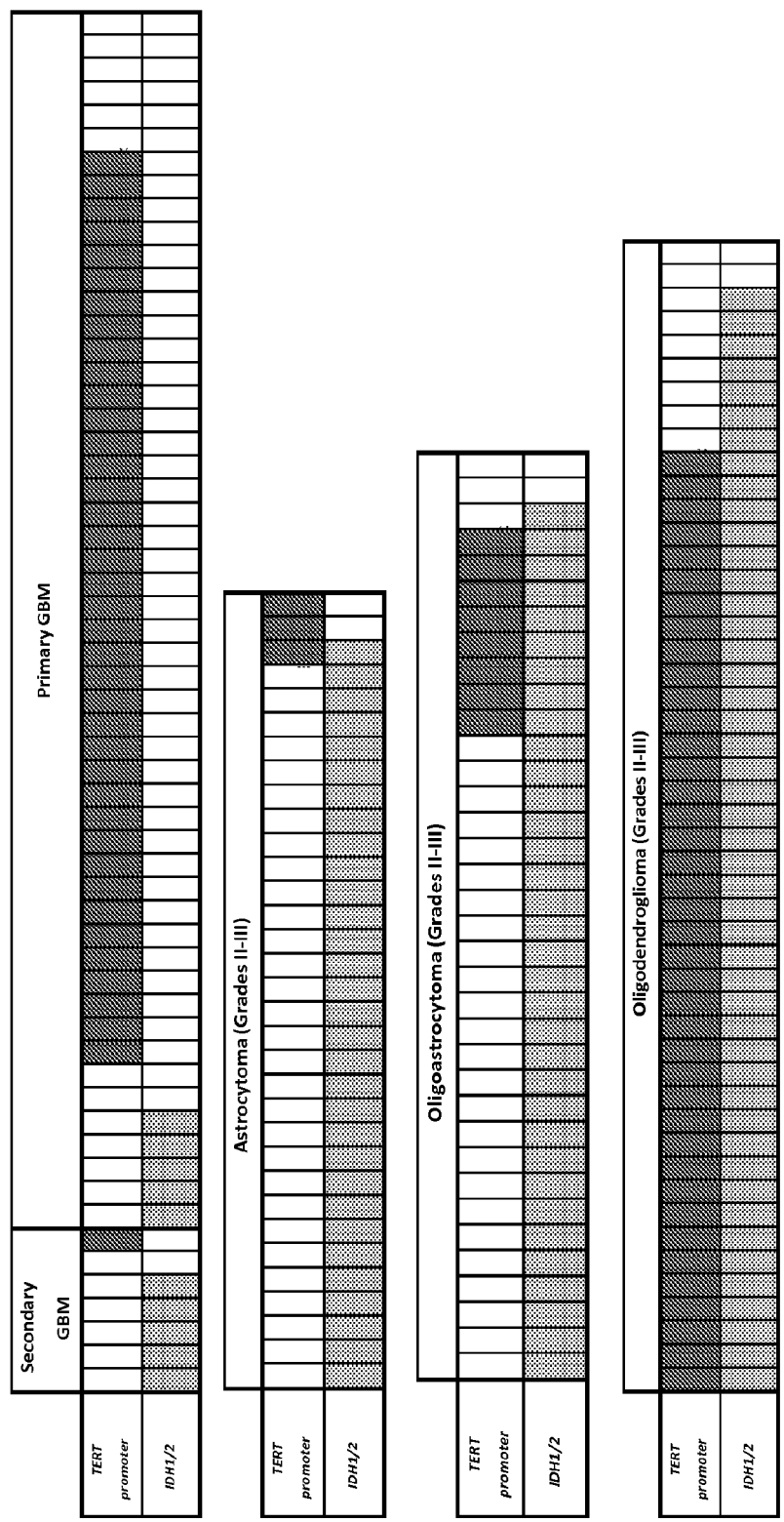
FIG. 3. TERT/IDH based genetic classification for diffuse glioma. The predominant genetic signatures include: $TERT^{MUT}IDH^{MUT}$, made up primarily of histologic oligodendrogliomas; $TERT^{WT}IDH^{MUT}$, made up of progressive astrocytomas; $TERT^{MUT}IDH^{WT}$, made up of primary GBMs; and $TERT^{WT}IDH^{WT}$, made up of GBMs. Red indicates TERT promoter mutation at either C228T or C250T; Green indicates mutation at either R132 of IDH1 or R172 of IDH2.
Figure 5:
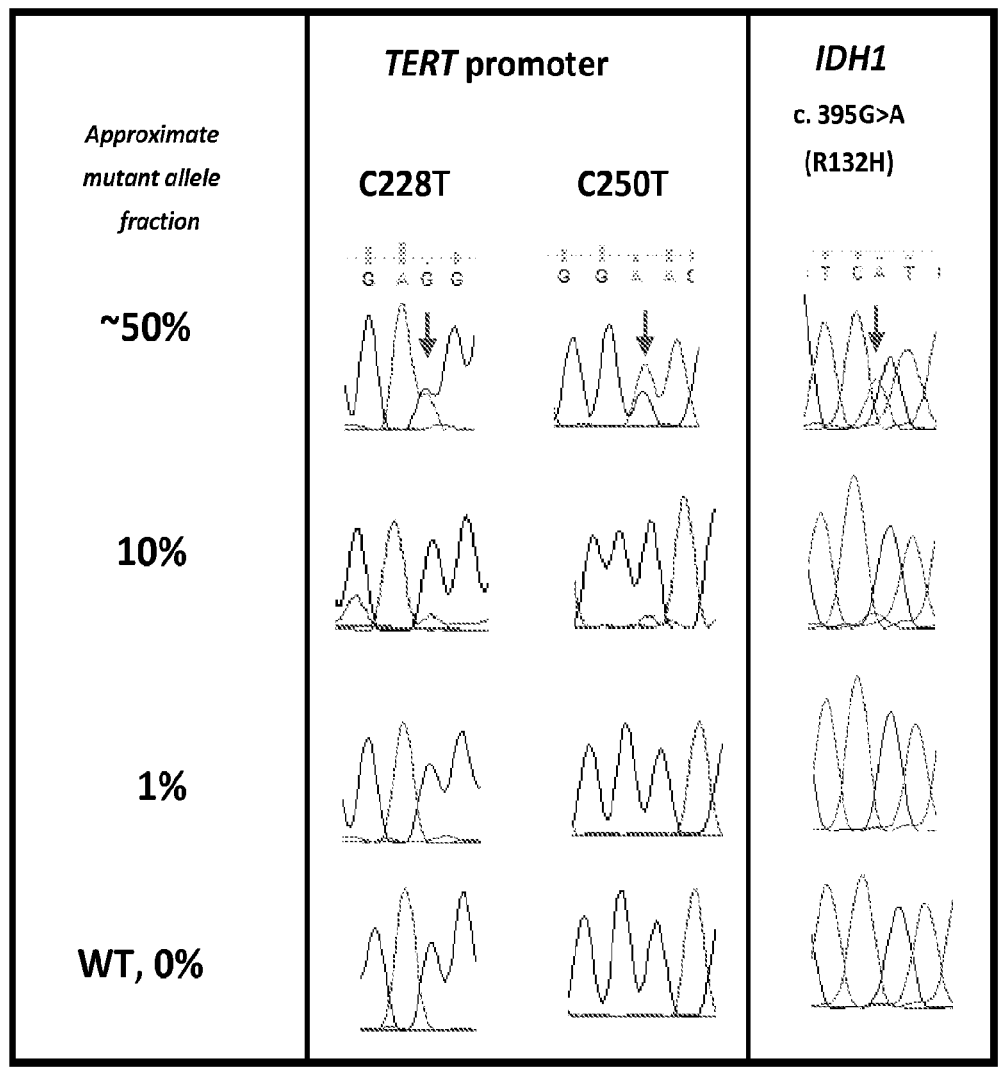
FIG. 5. Sanger sequencing chromatograms on dilutions of genomic DNA with specified mutation. At <20% mutant allele fraction, the peak for the mutant allele becomes indistinguishable from background, limiting use of this approach for clinical samples, in particular for diffuse glioma which is heterogeneous and invasive.

The inventors have developed a highly sensitive quantitative PCR (qPCR)-based assay that can detect the TERT promoter, IDH1/2 hotspot mutations swiftly, specifically, and sensitively. This qPCR-based diagnostic assay can detect mutant DNA in high backgrounds of normal DNA, such as when the mutant DNA is as low as 0.1% mutant alleles. This is a 200-fold higher sensitivity than traditional methods based on Sanger sequencing. Such detection limits are similar to other expensive, time consuming and complex techniques such as BEAMing, however the qPCR assay can be done in a matter of a few hours, requiring a single PCR step. Due to this assay's sensitivity, it permits detecting mutations in circulating tumor DNA (ctDNA). ctDNAs are often found in very limited amounts in the blood, urine, and CSF of cancer patients, but hold the promise of being used as a "liquid biopsy," through which patients can be diagnosed without surgical intervention. Tumor recurrence or drug resistance development can be monitored by examining these body fluids. The assay is not limited to using body fluids, however, and can similarly be used on more traditional tissue and biopsy samples.

This technology can be applied to detect hotspot mutations in IDH1, IDH2, TERT promoter mutations in DNA extracted from tumor tissues as well as from "liquid biopsy"

samples, including DNA extracted from CSF, plasma, serum, urine, and other body fluids. Further, the identification of these mutations is relevant not only to brain tumors, but also to many other tumor types in which these mutations are frequent, including liver and bladder cancer, skin cancers (melanoma, squamous and basal cell carcinoma), acute myeloid leukemia, cholangiocarcinoma, soft tissue tumors (echondroma, chondrosarcoma, spindle cell hemangioma, myxoid liposarcoma, atypical fibroxanthoma, myxoid liposarcoma) and thyroid cancer.

Body samples can be any convenient and expendable part of the body which contains tumor DNA. This may be a tumor tissue, margin tissue, biopsy sample, metastatic sample, lymph, cerebra spinal fluid, blood, including serum or plasma, urine saliva, mucus, and tears. Other fluids which drain a particular organ containing a tumor may also be sampled and tested. The DNA may be tested in the body sample, or it can be extracted using techniques known in the art. The DNA may be pre-amplified prior to the amplification to test for a mutation in TERT promoter, IDH1, and IDH2. The DNA may be depleted of extraneous sequences to render the target sequences a larger proportion of the analyte. The DNA that is tested may be genomic DNA, including without limitation mitochondrial DNA, amplified DNA, and cDNA.

As part of the assay, amplification cycles may be conducted at a higher temperature that is customary for PCR, to introduce a higher level of stringency and specificity. Higher temperatures may be at least 66° C., at least 67° C., at least 68° C., at least 69° C., at least 70° C., at least 71° C., at least 72° C., at least 73° C., at least 74° C., or at least 75° C., for example. Similarly, it may be desirable to conduct the pre-amplification step, if used, at such an elevated temperature. Low temperature amplification cycles can be used after initial higher temperature cycles. Low temperature cycles may be conducted at 60 degrees, at less than 60° C., at less than 59° C., at less than 58° C., at less than 57° C., at less than 56° C., at less than 55° C., at less than 54° C., at less than 53° C., at less than 52° C., or at less than 51° C., for example.

Multiplex reactions can be used in the assays if convenient in the particular setting. In a multiplex setting more than one set of primer pairs is used simultaneously in the same reaction mixture. In some cases it may be preferable to separate amplifications so that the reactions have less complexity, using fewer primer pairs, or even using a single primer pair. As described below, single reactions of the assay may use primer trios, e.g., having wild-type and mutant specific primers and a common primer. This can be considered a single reaction, rather than a multiplex for multiple different genomic segments.

LNA-modified nucleotides in the assays are typically used at the 3' end of primers to enhance specificity. The primers can also have additional sequences that are not complementary to the target genomic segments. The additional sequences or tags, can be used for convenience of assaying. As an example, and as discussed below, M13 sequences are added to the 5' end of the primers to facilitate sequencing of the amplicons formed using the primers. Tag sequences can be used as hybridization tags for identifying and/or quantifying. Tag sequences can be used for any additional functionality or for no functionality. Additional nucleotides complementary to the target can also be added to the 5' end of the primers with minimal effect on sensitivity.

High fidelity polymerases may be used to contribute to the accuracy of the amplification reactions. Many such polymerases are known in the art and can be selected by the skilled artisan. Exemplary DNA polymerases include FideliTaq™ DNA polymerase, Easy-A™ High-Fidelity PCR Cloning Enzyme, Herculase® II Fusion DNA Polymerase, Herculase® Enhanced DNA Polymerase, PfuUltra™ High-fidelity DNA Polymerase, ACCUZYME™ DNA Polymerase, VELOCITY™ DNA Polymerase, Vent™ (exo-) DNA Polymerase, KAPA HiFi HotStart™ DNA polymerase, and Pfx50™ DNA Polymerase.

While the mutations that are the targets of the assays are referred to as TERT C228T and C250T, the complement of these designations can also be assayed at the same position to assess the complementary nucleotides. Similarly for IDH1/IDH2 although R132 and R172 are mentioned throughout, the assay can be done on the complementary strand to detect the complementary nucleotides of the named mutations on the sense strand.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Figure 6:
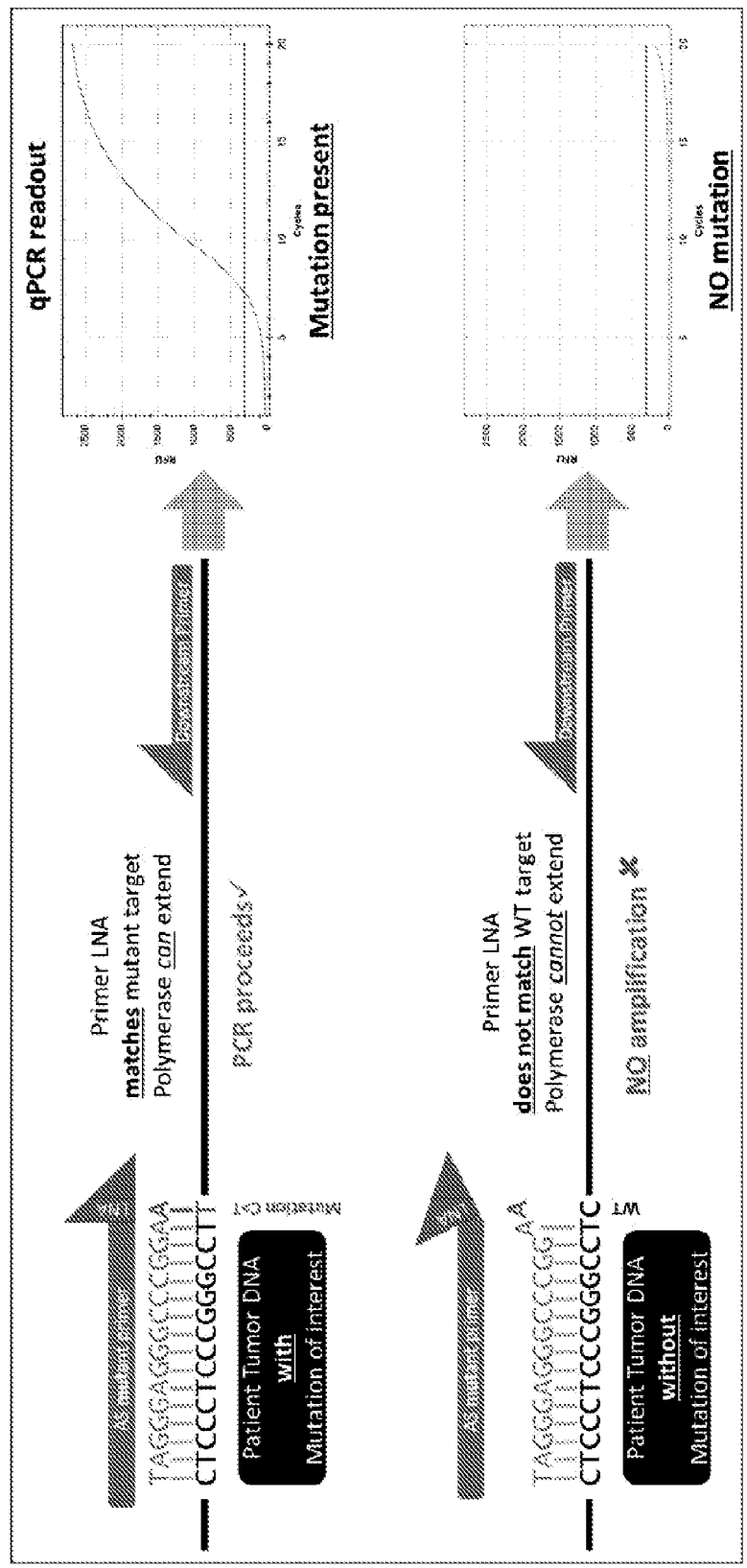
FIG. 6 is a schematic showing the overview of allele-specific qPCR using LNA primers. Antisense primer is SEQ ID NO: 30; mutant genomic DNA is SEQ ID NO: 31; wild-type genomic DNA is SEQ ID NO: 32.

TERT Promoter and IDH1/2 Hotspot Mutations AS LNA q-PCR Assay:

A. Background:

Allele-specific PCR is a form of DNA template amplification used for selective amplification of template containing a variation of interest and thus a method for SNP genotyping[18]. Most methods rely on discriminating primers that have higher complementarity to a target sequence with the genotype of interest. This is most often done by forcing the primer's 3' to be at the location of the mutation and complementary only to the target variant or wild type nucleotide. In this way, PCR efficiency is reduced when the primer binds to non-target alleles, delivering selective amplification (FIG. 6).

A major advance in this area has been the use of an alternate nucleic acid at the 3' end of these allele-specific primers known as locked nucleic acids (LNA). LNA is a nucleic acid analog with a methylene bridge between the 2'-O and 4'-C of a nucleic acid, which generates a bicyclic structure that locks the ribose moiety into a C3'-end conformation. This confirmation increases the $T_m$ when the LNA base hybridizes with its complement, greatly increasing the specificity of the primer for its target mutation or single nucleotide polymorphism (most sources measure at least 9 cycle greater difference LNA vs. DNA)[19]. This platform has been employed for allele discrimination in the context of identification of bacterial species[20], cystic fibrosis genetic alterations[19], BRAF mutations[21], HBV drug resistance mutations[22], mitochondrial mutations (in MELAS and NARP)[23], among other applications.

Although other approaches have been used for detecting mutations in the TERT promoter and IDH1/2 as alternatives to Sanger sequencing, including TaqMan LNA probes[24], High Resolution Melting Curve Analysis (traditional[25] and FRET-based[26]), SNaPshot[27,28], pyrosequencing[29], COLD PCR HRM[30], and SafeSeq[31], these techniques are either resource intensive or lack sensitivity and therefore are not practical as true clinical diagnostics.

B. TERT Promoter and IDH1/2 Hotspot Mutation AS LNA q-PCR Assay:

Primer Design

We have designed and tested a number of allele-specific primers for use as diagnostics for detection of the most frequent mutations in both the TERT promoter and IDH1/2 as well as their non-allele specific opposing primers needed for amplification (Table 1A). Of note, to establish these high performance, allele-specific (AS) primers we have designed over 10 different candidate AS primers which have varying length, forced mismatches introduced (3'-1 and -2 positions), and varied position of the LNA in an attempt to improve the discrimination of these primers. To test this discrimination ability, we used standard dilutions of tumor DNA in a background of normal DNA down to 15 copies or 0.1% and assessed the primers with the greatest ΔCt on qPCR while still producing a specific product. In addition, we have tested over 20 different candidate opposing primers again to produce a PCR product without background that specifically amplifies this region of the TERT promoter and that generates a small enough amplicon (<160 bp) capable of amplifying fragmented DNA sources (i.e., formaldehyde fixed paraffin embedded (FFPE), ctDNA). Other opposing primers also work with the candidate AS primers, however we have selected the smallest amplicons to facilitate qPCR (Table 1,2). Finally we have also developed similar allele-specific primers for the extremely rare IDH1 R132 mutations R132C,G,S,L) and IDH2 R172 mutations (R172M,W, G) however although these can be used, for application in glioma, the IDH1 R132H primer set is of most use.

TABLE 1A

High performance allele-specific primers for detection and quantification of most common TERT promoter (C228T, C250T), IDH1 (R132H), and IDH2 (R172K) hotspot mutations (*Note: + indicates). M13 tags (TGTAAAACGACGGCCAGT; SEQ ID NO: 28) and CAG GAA ACA GCT ATG ACC; SEQ ID NO: 29) were added to the 5' end of the common primers to facilitate sequencing.

| SEQ ID NO: | Primer Name | Primer Sequence (5' -> 3') | Length |
|---|---|---|---|
| 1 | TERT C228 AS LNA WT | CTGGGAGGGCCCGGA + G | 16 |
| 2 | TERT C228T AS LNA MUT | CTGGGAGGGCCCGGA + A | 16 |
| 3 | TERT C228 Common | GTCCTGCCCCTTCACCTTC | 19 |
| 4 | TERT C250 AS LNA WT | CCCGTCCCGACCCCT + C | 16 |
| 5 | TERT C250T AS LNA MUT | CCCGTCCCGACCCCT + T | 16 |
| 6 | TERT C250 Common 2 | CAGCGCTGCCTGAAACTC | 18 |
| 7 | IDH1 R132 AS LNA WT | GGGTAAAACCTATCATCATAGGTC + G | 25 |
| 8 | IDH1 R132H AS LNA MUT | GGGTAAAACCTATCATCATAGGTC + A | 25 |
| 9 | IDH1 R132 Common | AACATGCAAAATCACATTATTGCC | 24 |
| 10 | IDH1 R132 Common 2 | ATCCCCCGGCTTGTGAGT | 18 |
| 11 | IDH2 R172 AS LNA WT | AAGCCCATCACCATTGGCA + G | 20 |
| 12 | IDH2 R172K AS LNA MUT | AAGCCCATCACCATTGGCA + A | 20 |
| 13 | IDH2 R172 Common | AGGTCAGTGGATCCCCTCTC | 20 |
| 14 | IDH2 R172 Common 2 | GGACCAAGCCCATCACCATT | 20 |

TABLE 1B

High performance allele-specific primers for detection of rare IDH1 and IDH2 mutations (note these primer sets use the same opposing Common primers as in 1A).

| SEQ ID NO: | Primer Name | Primer Sequence (5' -> 3') | Length |
|---|---|---|---|
| 15 | IDH1 R132C AS LNA MUT | GGGTAAAACCTATCATCATAGGT + T | 24 |
| 16 | IDH1 R132G AS LNA MUT | GGGTAAAACCTATCATCATAGGT + G | 24 |
| 17 | IDH1 R132S AS LNA MUT | GGGTAAAACCTATCATCATAGGT + A | 24 |
| 18 | IDH1 R132L AS LNA MUT | GGGTAAAACCTATCATCATAGGTC + T | 25 |
| 19 | IDH2 R172M AS LNA MUT | AAGCCCATCACCATTGGCA + T | 20 |
| 20 | IDH2 R172W AS LNA MUT | AAGCCCATCACCATTGGC + G | 19 |
| 21 | IDH2 R172G AS LNA MUT | AAGCCCATCACCATTGGC + T | 19 |

TABLE 2

Primer sets for allele-specific qPCR assay for genotyping the TERT promoter and IDH1/2

| Primer 1 | Primer 2 | Target size | Amplicon size* | Purpose |
|---|---|---|---|---|
| TERT: C228 and C250 | | | | |
| TERT C228 AS LNA WT or C228T AS LNA MUT | TERT C228 Common | 101 bp | 119 bp | WT/MUT TERT C228 Detection |
| TERT C250 AS LNA WT or C250T AS LNA MUT | TERT C250 Common 2 | 115 bp | 133 bp | WT/MUT TERT C250 Detection |
| TERT C228 Common | TERT C250 Common 2 | 163 bp | 199 bp | TERT promoter copy number/normalization. Pre-amplification of TERT promoter |
| IDH1: R132 | | | | |
| IDH1 R132 AS LNA WT or R132H AS LNA MUT | IDH1 R132 Common | 80 bp | 98 bp | WT/MUT R132 Detection |
| IDH1 R132 Common 2 | IDH1 R132 Common | 102 bp | 138 bp | IDH1 exon 4 copy number/normalization. Pre-amplification of IDH1. |
| IDH2: R172 | | | | |
| IDH2 R172 AS LNA WT or R172K AS LNA MUT | IDH2 R172 Common | 72 bp | 90 bp | WT/MUT R172 Detection |
| IDH2 R172 Common 2 | IDH2 R172 Common | 77 bp | 113 bp | IDH2 exon 4 copy number/normalization. Pre-amplification of IDH2. |

*Note
target regions amplified are 18 bp shorter for AS amplicons and 36 bp shorter for non-AS amplicons due to M13 sequence tags added C. High Performance PCR Program and Reagents The PCR program and reagents efficiently amplify the TERT promoter and IDH1/2 exon 4 both in an allele-specific and non-AS fashion and in two different contexts: (1) PCR of genomic DNA and (2) nested PCR of pre-amplified genomic DNA. For applications in which mutation status is needed rapidly and there is sufficient sample to perform PCR with replicates, the first program is recommended. For applications in which there is limited DNA or the DNA is of poor quality, the second program is recommended.

a. 1-Step AS-LNA qPCR of Genomic DNA for TERT/IDH Status

It is challenging to create a PCR program to allow for efficient allele-specific PCR in particular because of the limitation in location of the primers. The TERT promoter is notoriously challenging to amplify due to its high GC content (>80% through the region of interest and 88% in the stretch from C228 to C250) and repetitive sequence (10 runs of 4G's in the region of interest). For maximum discrimination between wildtype and mutant alleles, the amplification program we employ uses an initial phase of amplification at a high annealing temperature (≥66° C.) followed by a second phase of amplification at a lower annealing temperature (≤60° C.). This program on our thermocycler with ramp rate 5° C./sec, takes <1 hour excluding the melt curve (Table 3). This can be adjusted with shorter denaturation with higher temperature (e.g., 1 min at 98° C.) and shorter annealing times to facilitate even more rapid detection, which may be applicable in scenarios of intraoperative diagnosis. We have also used traditional single annealing temperature programs, which work best at higher annealing temperatures (≥66° C.), but they are less sensitive. Below we have listed the program for maximum discrimination that works best for all primer sets. Allele-specific (AS) primers were purchased from Exiqon (Woburn, Mass., USA) as custom oligonucleotides that had been subjected to dual HPLC purification. Non-AS primers were purchased from IDT (Coralville, Iowa, USA) as custom oligonucleotides with standard purification

TABLE 3

PCR program 1 for AS-qPCR based genotyping

| | Stage | Temperature | Duration | cycles |
|---|---|---|---|---|
| Step 1 | Initial Denaturation | 95° C. | 180 s | 1 x |
| Step 2 | Denaturation | 95° C. | 15 s | 19 x |
| Step 3 | Annealing #1 | 68° C. | 20 s | |
| Step 4 | Denaturation | 95° C. | 15 s | 20-30 x |
| Step 5 | Annealing #2 | 57.6° C. | 20 s | |
| Step 6 | Melt Curve | 65° C.-95° C. | increase 0.5° C./5 s | |

NOTE: Plate reads occur at Step 5 and Step 6 (FAM)

The reaction conditions for this PCR are shown in Table 4. Many GC-rich kits and other polymerases were used and had difficulties in particular with the TERT promoter. The read out for our assay is a SYBR green signal, using the KAPA SYBR Fast 2X MasterMix (KK4600, Boston, Mass., USA). The primer concentration has been varied and works across a large range of concentrations. Additionally, input >50 ng can be used, but begins to inhibit the reaction.

TABLE 4

PCR reagents for 1-step qPCR using SYBR for TERT/IDH mutation detection

|  | Final concentration |
|---|---|
| KAPA SYBR FAST 2X MasterMix | 1 X |
| dH2O | Up to 15 μL |
| Primer 1 (10 μM) | 400 nM |
| Primer 2 (10 μM) | 400 nM |
| Template | 1-50 ng |
| Total | 15 μL | b. Nested AS LNA qPCR of Pre-Amplified DNA for TERT/IDH Status

A second approach for mutation detection is a nested qPCR approach that works very well for: low quality samples (i.e., ctDNA, FFPE gDNA), and samples of low analyte quantity that are insufficient for necessary replicates (i.e., fine needle biopsies). This nested qPCR assay also has highly reliable quantification as PCR inhibition and differences in primer efficiencies are much less significant in a nested PCR context. To use this approach, the locus of interest is amplified with a non-biased (NB) primer set in TERT promoter, IDH1, or IDH2, or all three in a multiplex fashion, using a high fidelity enzyme for limited cycle number (<20 cycles) at a high annealing temperature (≥66° C.) (Table 5,6). Then, the resulting PCR product is purified (either using column-based or bead-based approach) and diluted (usually 1:1000) and serves as the template for the next round of amplification, which is using the allele-specific LNA-modified primers described above. The nested PCR is performed at an annealing temperature ≥66° C. as this offers the highest discrimination (Table 7, 8). The benefit of this nested approach is that there is a much greater supply of template, all generated from 1-50 ng of gDNA, which can be screened for many more mutations than would otherwise be possible. Below we describe the high performance PCR programs for nested qPCR. It is beneficial to split pre-amplification reactions into multiple reactions (e.g., 50 μl split into 5×10 μl), which can then be pooled. Following this step, one can purify PCR products using a column or bead-based approach.

TABLE 5

PCR program for high-fidelity pre-amplification

|  | Stage | Temperature | Duration | cycles |
|---|---|---|---|---|
| Step 1 | Initial Denaturation | 95° C. | 180 s | 1 x |
| Step 2 | Denaturation | 98° C. | 15 s | |
| Step 3 | Annealing #1 | 68° C. | 20 s | 20 x |
| Step 4 | Extension | 72° C. | 2 s | |
| Step 5 | Storage | 4° C. | 20 s | |

TABLE 6

PCR reagents for high fidelity pre-amplification of TERT/IDH loci

|  | Final concentration |
|---|---|
| KAPA SYBR FAST | 1 X |
| KAPA HiFi HotStart DNA polymerase | 1 unit |

TABLE 6-continued

PCR reagents for high fidelity pre-amplification of TERT/IDH loci

|  | Final concentration |
|---|---|
| 10 mM dNTP mix | 0.3 mM each |
| dH2O | Up to 15 μL |
| Primer 1 (10 μM) | 200-500 nM |
| Primer 2 (10 μM) | 200-500 nM |
| Template | 1-50 ng |
| Total | 50 μL |

TABLE 7

PCR program for nested Allele-Specific qPCR of Non Bias PCR product

|  | Stage | Temperature | Duration | cycles |
|---|---|---|---|---|
| Step 1 | Initial Denaturation | 95° C. | 3-5 min | 1 x |
| Step 2 | Denaturation | 95° C. | 15 s | |
| Step 3 | Annealing #1 | 69° C. | 20 s | 40-50x |
| Step 4 | Extension | 72° C. | 1 s | |
| Step 5 | Melt Curve | 65 ° C.-95° C. | increase 0.5° C./5 s | Only if using SYBR |

Plate read occurs at step 3, and if using SYBR and a melt curve, step 5 for FAM/SYBR

TABLE 8

PCR reagents for allele-specific qPCR using LNA modified primers

|  | Final concentration |
|---|---|
| KAPA SYBR Fast/KAPA PROBE Fast/KAPA PROBE FORCE, all 2X | 1X |
| Probe (10 μM) (if probe used instead of SYBR) | 250 nM |
| Primer 1 (10 μM) | 500 nM |
| Primer 2 (10 μM) | 500 nM |
| dH2O | Up to 25 μl |
| Template | 1-50 ng |
| Total | 25 μL |

If using a probe for detection in nested qPCR, the protocol should use either of the two probe mixtures mentioned in Table 8 and either of these probes depending on TERT or IDH detection: TERT probe: /56FAM/CGGGTCCCC/ZEN/GGCCCAGC/3IaBkFQ/(SEQ ID NO: 22-23); IDH1 probe: /56-FAM/ATGACTTAC/ZEN/TTGATC-CCCATAAGCATGA/3IABkFQ/ (SEQ ID NO: 24-25). The TERT probe is designed in the common region between C228T and C250T, whereas the IDH1 probe is designed in the region between the allele-specific primer and the common primer, and as such can be used for all allele-specific IDH reactions (R132S, C, L, G and H).

D. Standards, Copy Number and Mutation % Quantification

Alongside the AS TERT and IDH1/2 primer sets, we use primers to amplify in a non-allele-specific fashion the TERT promoter region surrounding the two mutations (C228T and C250T), IDH1 exon 4 surrounding the R132H mutation, and also primers designed to amplify the highly repetitive human line-1 elements (hline1Fwd: 5' TCACTCAAAGCCGCT-CAACTAC-3' (SEQ ID NO: 26), hline1Rev: 5'-TCTGCCT-TCATTTCGTTATGTACC-3') (SEQ ID NO: 27). This information can be used to normalize the Ct value from allele-specific PCR amplifying the WT or MUT allele and provide a quantitative readout of the mutant allele fraction, enabling cross comparison of samples. As is mentioned in section E, this is not necessary if samples are all at identical concentrations. In addition to this, a number of standardized samples are run alongside tested samples for the purpose of validation, including samples such as: 50% mutant sample (positive control), 1% mutant sample (low mutation positive control), 0% wildtype sample (negative control), and a no template control. These standards were generated by isolation of genomic DNA (gDNA) from cell lines with known TERT/IDH status. As an example, we use gDNA from the following cell lines: DAOY (C228T), A375 (C250T), HCT116 (wildtype) and HCT116 IDH1 R132H knockin #2 (IDH1 R132H). Dilution of these samples with gDNA wildtype at the target locus yields the 1% and lower standards needed. Another source of standard is plasmid DNA with the target mutations, which we have generated as "100% standards" using TOPO cloning (K4810-01, Life technologies). We used inserts generated by PCR amplification of a portion of the TERT promoter/IDH1/2 from tumor samples with the mutations of interest. Additionally, to serve as a more realistic quantitative control, we have generated a perfect heterozygote plasmid with both the TERT and IDH1 mutations of interest (see details below, FIG. 7), which can be expanded to other target mutations by cloning these loci into the same plasmid or in a similar fashion into independent plasmids.

Each primer set is run in triplicate on the samples. An example run for detecting the mutant alleles for TERT and IDH1 (i.e., the most common glioma-related mutations) is using the following primer sets in Table 9. The wildtype AS primer sets can also be used as an alternative to the non-biased (NB) amplicons for more accurate quantification. Primers for non-biased amplicons show no specificity for a particular allele (mutant or wild type) and should amplify both types of alleles equally.

tant from each other to ensure limited primer interference. These standards were generated by first designing genes for synthesis by GENEWIZ where the portion of the TERT promoter (the 228 and 250 loci+/−~150 bp) and the portion of the IDH1 exon 4 (R132 or c.395G locus+/−~150 bp) in pUC-57-ampR plasmids, along with synthetic restriction enzyme sites separating each gene fragment in case of desire to separate the loci from each other (some authors cite this as improving its performance as a standard). These were cloned into the vector pGL3-enh (Promega) which is only used as it has cloning sites that are approximately equidistant from each other, ensuring that the two TERT-IDH blocks making up the "heterozygote" are maximally separated. Additionally we generated an equivalent plasmid where all loci were wildtype as a negative control, with two copies of each gene locus. This system can be expanded to other mutations of interest, for example rarer IDH1 mutations and IDH2 mutations. We have introduced restriction enzyme sites surrounding each locus to facilitate expansion with other loci and to enable selective linearization.

E. Data Analysis

Figure 9:
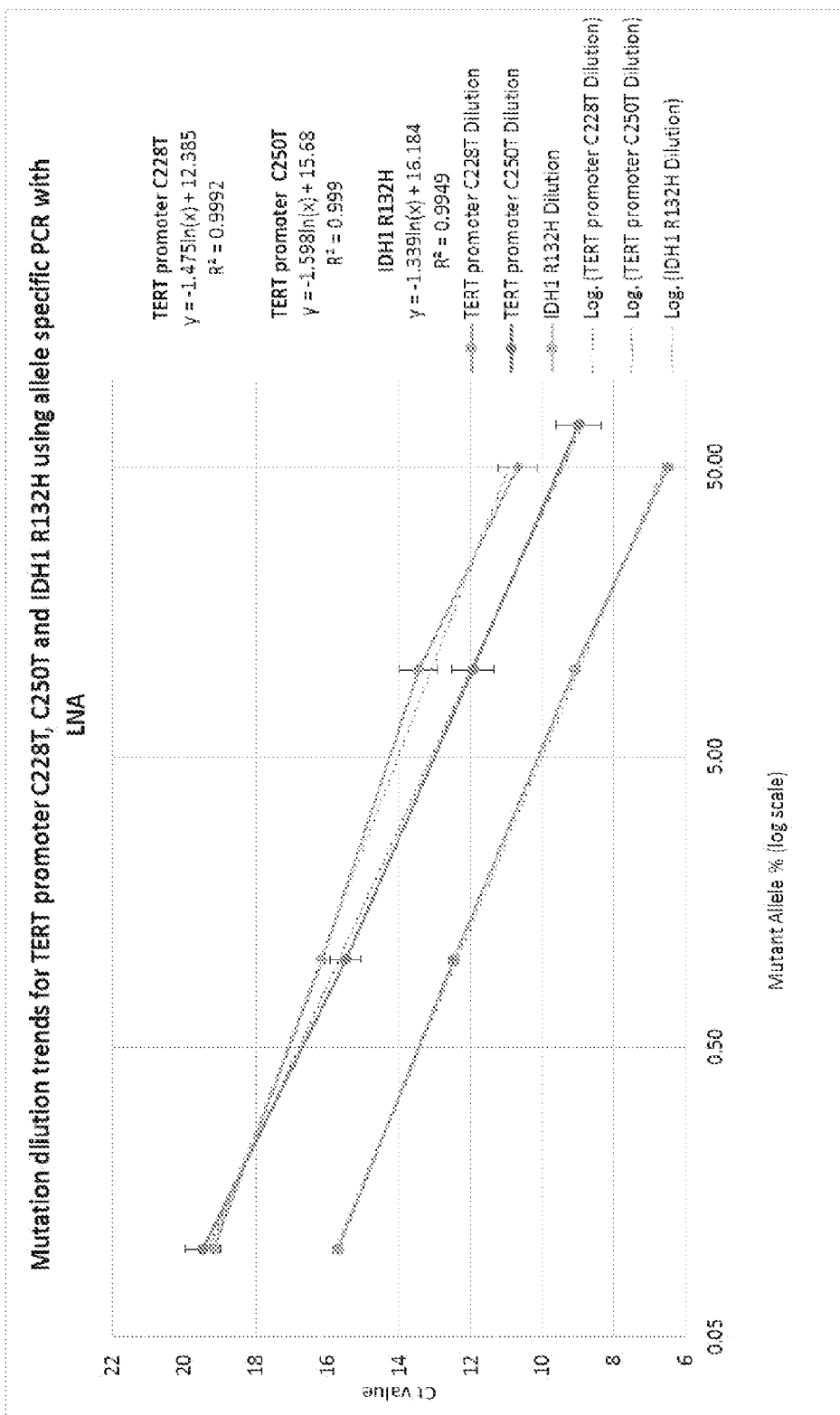

There are several options for data analysis. One approach that is most straightforward is to ensure all samples have equal concentrations and use a trend-line generated from the dilution of standard cell line DNA to various mutation percentages to back-calculate the mutant allele fraction (FIG. 9). As shown below, the trend-lines have excellent linearity ($R^2 > 0.994$).

For use of samples with varying DNA input amounts, we have employed approaches that normalize the Ct value to a measurement of the sample's copy number (using Ct value of the non-bias/common amplicon or of hline1), and use the positive control sample as a mutant allele percentage standard. (The Ct (cycle threshold) is defined as the number of cycles required for the fluorescent signal to cross the threshold (ie exceeds background level). This type of normalized calculation additionally requires an estimation of the primer

TABLE 9

Primer combinations for testing for TERT promoter C228T, C250T and IDH1 R132H

| Primer combination | Forward Primer Name | Reverse Primer Name | Purpose |
|---|---|---|---|
| TERT AS 228 MUT | TERT C228T AS LNA MUT | TERT C228 Common | TERT promoter C228T detection and quantification |
| TERT AS 250 MUT | TERT C250T AS LNA MUT | TERT C250 Common 2 | TERT promoter C250T detection and quantification |
| TERT NB | TERT C228 Common | TERT C250 Common 2 | Reference for copy number at TERT promoter locus |
| IDH1 R132H AS MUT | IDH1 R132H AS LNA MUT | IDH1 R132 Common | IDH1 R132H detection and quantification |
| IDH1 NB | IDH1 R132 Common | IDH1 R132 Common 2 | Reference for copy number at IDH1 |
| hline1 | hline1 forward | hline1 reverse | Reference for copy number using line1 elements, do not use with nesting |

Figure 7:
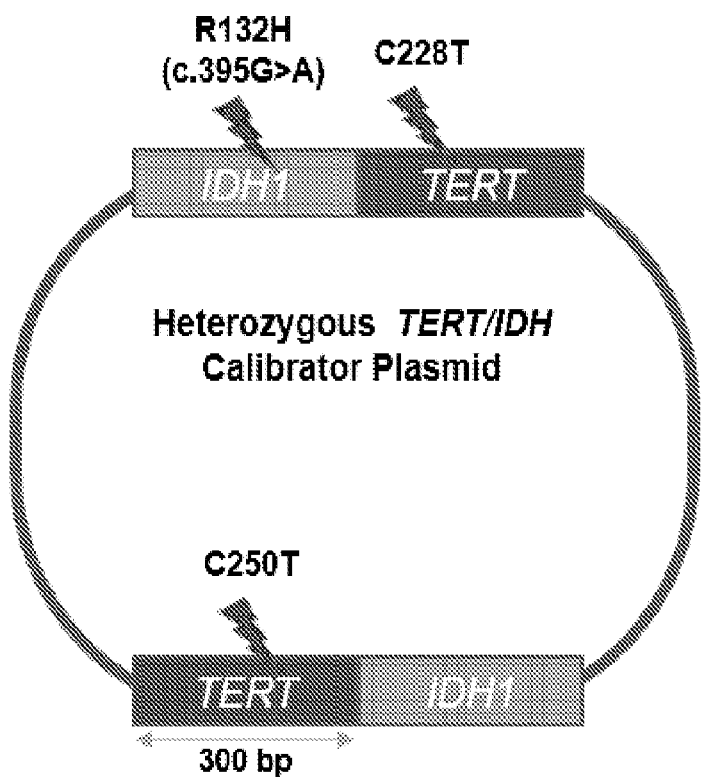
FIG. 7 is a schematic drawing showing TERT promoter C228/C250T and IDH1 R132H heterozygous calibrator plasmid based on PGL3-enh vector. TERT C228T, C250T and IDH1 R132H are present in ratios of 50% in each plasmid, with 300 bp of each target cloned into pGL3-enh plasmid. Loci are distanced 3 kb from each other to limit cross reactivity of primers. Additional genetic loci of interest can be added alongside these segments to generate reproducible mutant allele fractions of mutations.
Figure 8:
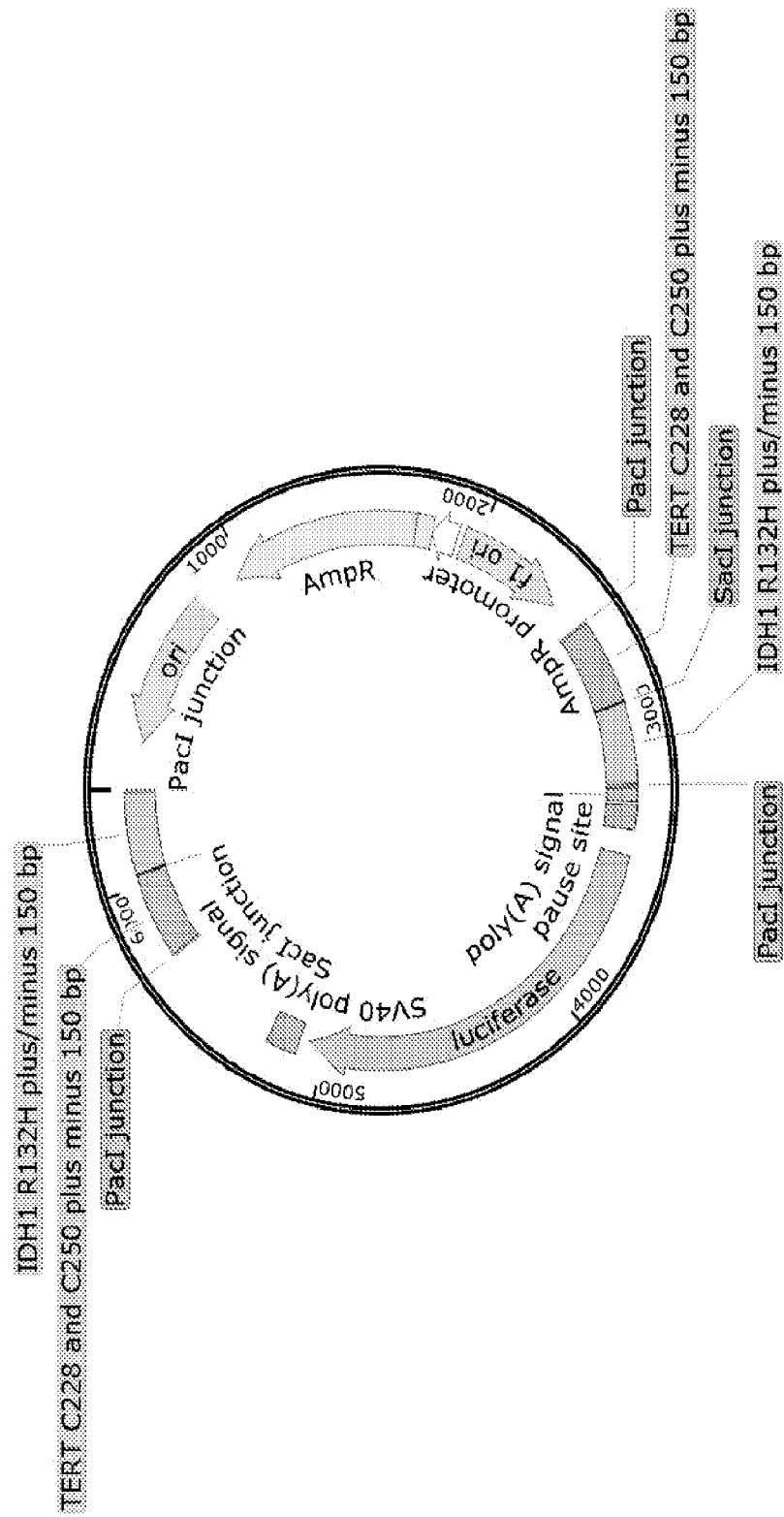
FIG. 8. Detailed schematic of TERT promoter C228T/C250T and IDH1 R132H heterozygous calibrator plasmid, cloned into sites ~3 kb away from each other in pg13-enh vector FIG. 9. Dilution of target mutation to varying mutant allele fractions (10%, 1%, 0.1%). Across these ranges, the allele-specific assays show excellent linearity ($R^2$>0.994).

We designed the heterozygote calibrator to serve as a 50% mutation/50% WT sample, as dilutions can only approximate relative ratios of mutant and wildtype allele fractions. This standard works best as a standard for the nested PCR approach mentioned previously. A heterozygous calibrator plasmid has been previously generated for single mutations, such as BRAF V600E mutation[32], however here we made a single calibrator for multiple mutations: IDH1 R132H and TERT C228T/C250T, greatly facilitating quantification and workflow (FIG. 7). The two target regions are separated by >3100 bp and the respective mutations are roughly equidisefficiency. Based on dilutions of genomic DNA, we have estimated the primer efficiencies for each primer combination (Table 10).

TABLE 10

Primer combinations and their efficiencies

| Primer Combination Name | Efficiency |
|---|---|
| TERT C228T AS LNA MUT + TERT C228 Common | 106.5% |

TABLE 10-continued

Primer combinations and their efficiencies

| Primer Combination Name | Efficiency |
|---|---|
| TERT C250T AS LNA MUT + TERT C250 Common 2 | 91.80% |
| TERT C228 Common + TERT C250 Common 2 | 82.33% |
| IDH1 R132H AS LNA MUT + IDH1 R132 Common | 105.8% |
| IDH1 R132 Common + IDH1 R132 Common 2 | 91.05% |

The triplicate Ct values are averaged for each primer set and normalized by primer efficiency values. For each sample, the average Ct value for the AS mutant primers are then normalized by the average Ct value for the respective common (NB) primer set. Using the equation below (by Pfaffl et al.), where $E_{AS}$ refers to the efficiency of the AS mutant primer combination, control refers to the mean Ct value for the positive control of known mutation percentage (in this case 50%), and sample refers to the mean Ct value for the sample being assessed. The same information is in the denominator, but all with reference to the appropriate NB primer set being used for normalization (e.g., TERT common, IDH1 common, line 1). For more accurate values, we recommend adjusting the equation using the AS mutant vs. AS wildtype for comparison, which yields a ratio of mutant: wildtype allele fraction which can be adjusted to yield the mutant allele fraction alone.

$$\text{Mutant allell \%} = \frac{(E_{AS})^{\Delta Ct(50\% \text{ control-sample})}}{(E_{NB})^{\Delta Ct(50\% \text{ control-sample})}}$$

These approaches work for both allele-specific qPCR of gDNA and nested qPCR of pre-amplified, purified PCR product. In the context of nesting qPCR, we recommend using the pre-amplified heterozygous calibrator plasmid as a highly accurate standard with 50% of each target mutation, and normalizing to this as the reference, although pre-amplified genomic DNA of known mutation percentage can also be used.

F. Performance

Figure 10:
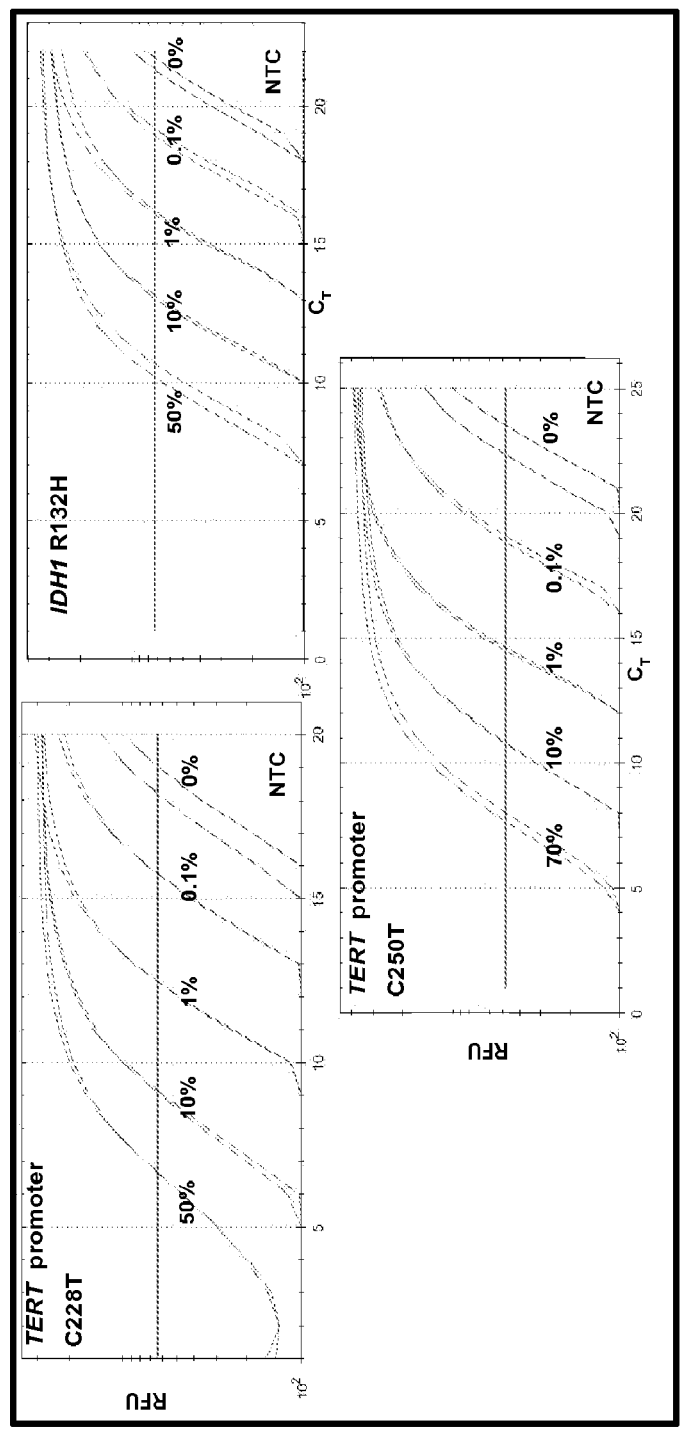
FIG. 10. TERT/IDH Allele-specific LNA qPCR test detects 0.1% mutant allele fraction (~15 mutant copies).
Figure 11:
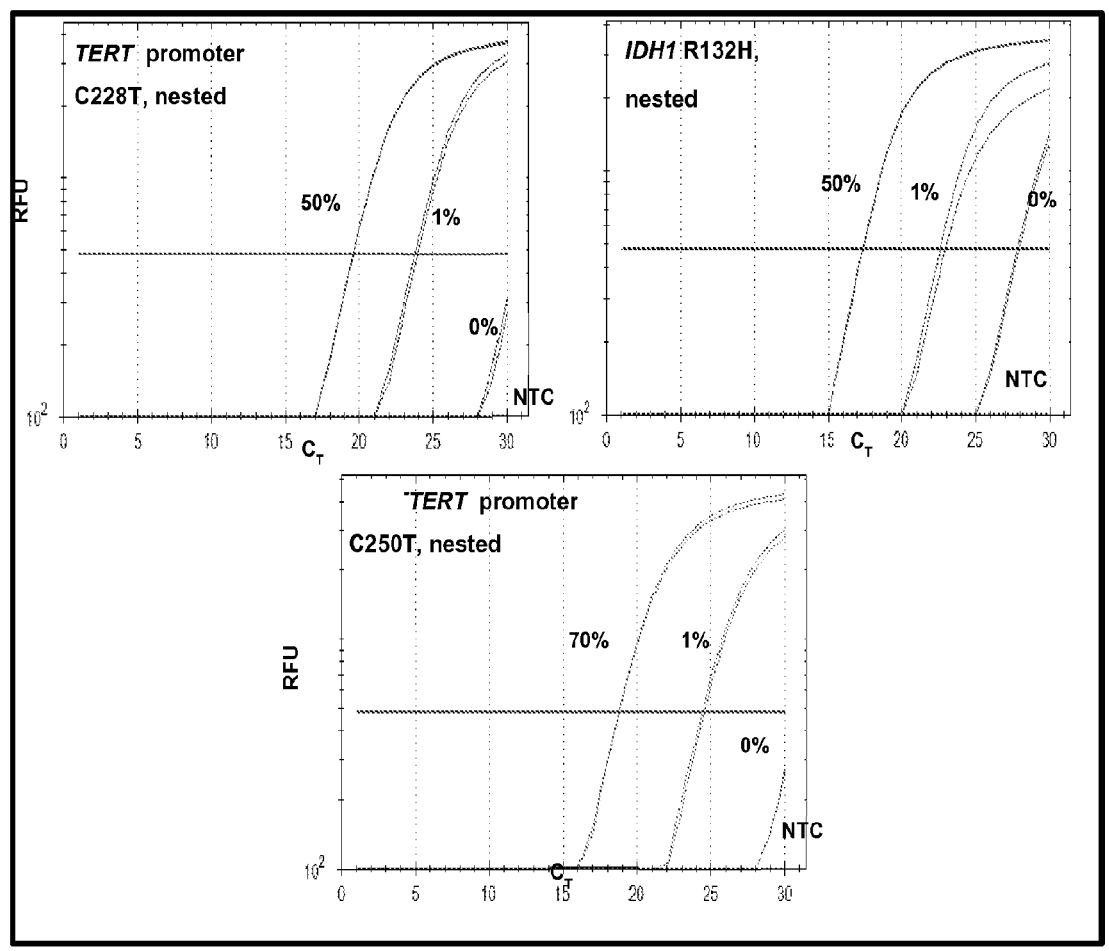
FIG. 11. TERT/IDH Allele-specific LNA qPCR in nested format retains high discrimination, while using only 50 ng of gDNA pre-amplified as a template.

Using the above primer sets and conditions, we have tested the limit of detection of these primers in high levels of background and found that it can reliably detect down to 15 mutant genomic DNA copies in a background of 15,000 wildtype copies (0.1%), and distinguishes this from 0% (wildtype) samples (FIG. 10). Using nested qPCR, high discrimination can also be achieved with allele-specific PCR (FIG. 11).

G. Application of the qPCR Diagnostic

To test our assay in a clinically relevant context, we have taken DNA from 43 glioma samples that have been previously genotyped using Sanger sequencing and identified using this method as TERT promoter WT and IDH1 R132 WT. We used our qPCR assay and identified 9 samples with TERT promoter C228T mutations and 3 samples with IDH1 R132H mutations, totaling 12 samples or 28% of the total, all with percentages <10% that had been previously undetectable by traditional methods (Table 11). In addition, this assay was completed within ~1 hr with quantitative results, whereas Sanger sequencing involves an additional sequencing step following PCR.

TABLE 11

Cases with low level mutations detected by qPCR but not by Sanger sequencing (false negatives).

| Case ID | TERT Sanger | TERT qPCR | Histology |
|---|---|---|---|
| A | WT | C228T | GBM |
| B | WT | C228T | GBM |
| C | WT | C228T | GBM |
| D | WT | C228T | Anaplastic Astrocytoma |
| E | WT | C228T | GBM |
| F | WT | C228T | GBM |
| G | WT | C228T | GBM |

| Case ID | IDH1 Sanger | IDH1 qPCR | Histology |
|---|---|---|---|
| H | WT | R132H | Astrocytoma |
| K | WT | R132H | Astrocytoma |

REFERENCES

The disclosure of each reference cited is expressly incorporated herein.

1. Yan, H. et al. IDH1 and IDH2 mutations in gliomas. *N Engl J Med* 360, 765-73 (2009).
2. Jansen, M., Yip, S. & Louis, D. N. Molecular pathology in adult gliomas: diagnostic, prognostic, and predictive markers. *Lancet Neurol* 9, 717-26 (2010).
3. Louis, D. N., International Agency for Research on Cancer, World Health Organization.
   & Deutsches Krebsforschungszentrum Heidelberg. *WHO classification of tumours of the central nervous system*, 309 p. (International Agency for Research on Cancer: Distributed by WHO Press, World Health Organization, Lyon Geneva, Switzerland, 2007).
4. Ostrom, Q. T. et al. CBTRUS statistical report: primary brain and central nervous system tumors diagnosed in the United States in 2007-2011. *Neuro Oncol* 16 Suppl 4, iv1-63 (2014).
5. Ohgaki, H. & Kleihues, P. The definition of primary and secondary glioblastoma. *Clin Cancer Res* 19, 764-72 (2013).
6. Coons, S. W., Johnson, P. C., Scheithauer, B. W., Yates, A. J. & Pearl, D. K. Improving diagnostic accuracy and interobserver concordance in the classification and grading of primary gliomas. *Cancer* 79, 1381-93 (1997).
7. Killela, P. J. et al. TERT promoter mutations occur frequently in gliomas and a subset of tumors derived from cells with low rates of self-renewal. *Proc Natl Acad Sci USA* 110, 6021-6 (2013).
8. Jiao, Y. et al. Frequent ATRX, CIC, FUBP1 and IDH1 mutations refine the classification of malignant gliomas. *Oncotarget* 3, 709-22 (2012).
9. Heaphy, C. M. et al. Altered telomeres in tumors with ATRX and DAXX mutations. *Science* 333, 425 (2011).
10. Bettegowda, C. et al. Mutations in CIC and FUBP1 contribute to human oligodendroglioma. *Science* 333, 1453-5 (2011).
11. Killela, P. J. et al. Mutations in IDH1, IDH2, and in the TERT promoter define clinically distinct subgroups of adult malignant gliomas. *Oncotarget* (2014).
12. Amary, M. F. et al. IDH1 and IDH2 mutations are frequent events in central chondrosarcoma and central and periosteal chondromas but not in other mesenchymal tumours. *J Pathol* 224, 334-43 (2011).

13. Pansuriya, T. C. et al. Somatic mosaic IDH1 and IDH2 mutations are associated with enchondroma and spindle cell hemangioma in Ollier disease and Maffucci syndrome. *Nat Genet* 43, 1256-61 (2011).
14. Kipp, B. R. et al. Isocitrate dehydrogenase 1 and 2 mutations in cholangiocarcinoma. *Hum Pathol* 43, 1552-8 (2012).
15. Mardis, E. R. et al. Recurring mutations found by sequencing an acute myeloid leukemia genome. *N Engl J Med* 361, 1058-66 (2009).
16. Borger, D. R. et al. Frequent mutation of isocitrate dehydrogenase (IDH)1 and IDH2 in cholangiocarcinoma identified through broad-based tumor genotyping. *Oncologist* 17, 72-9 (2012).
17. Davidson, C. J. et al. Improving the limit of detection for Sanger sequencing: A comparison of methodologies for KRAS variant detection. *Biotechniques* 2012 (2012).
18. Wu, D. Y., Ugozzoli, L., Pal, B. K. & Wallace, R. B. Allele-specific enzymatic amplification of beta-globin genomic DNA for diagnosis of sickle cell anemia. *Proc Natl Acad Sci USA* 86, 2757-60 (1989).
19. Latorra, D., Campbell, K., Wolter, A. & Hurley, J. M. Enhanced allele-specific PCR discrimination in SNP genotyping using 3' locked nucleic acid (LNA) primers. *Hum Mutat* 22, 79-85 (2003).
20. Rupp, J., Solbach, W. & Gieffers, J. Single-nucleotide-polymorphism-specific PCR for quantification and discrimination of *Chlamydia pneumoniae* genotypes by use of a "locked" nucleic acid. *Appl Environ Microbiol* 72, 3785-7 (2006).
21. Morandi, L. et al. Allele specific locked nucleic acid quantitative PCR (ASLNAqPCR): an accurate and cost-effective assay to diagnose and quantify KRAS and BRAF mutation. *PLoS One* 7, e36084 (2012).
22. Zeng, Y. et al. Establishment of real time allele specific locked nucleic acid quantitative PCR for detection of HBV YIDD (ATT) mutation and evaluation of its application. *PLoS One* 9, e90029 (2014).
23. Strand, H., Ingebretsen, O. C. & Nilssen, O. Real-time detection and quantification of mitochondrial mutations with oligonucleotide primers containing locked nucleic acid. *Clin Chin Acta* 390, 126-33 (2008).
24. Remke, M. et al. TERT promoter mutations are highly recurrent in SHH subgroup medulloblastoma. *Acta Neuropathol* 126, 917-29 (2013).
25. Patel, K. P. et al. Diagnostic testing for IDH1 and IDH2 variants in acute myeloid leukemia an algorithmic approach using high-resolution melting curve analysis. *J Mol Diagn* 13, 678-86 (2011).
26. Horbinski, C., Kelly, L., Nikiforov, Y. E., Durso, M. B. & Nikiforova, M. N. Detection of IDH1 and IDH2 mutations by fluorescence melting curve analysis as a diagnostic tool for brain biopsies. *J Mol Diagn* 12, 487-92 (2010).
27. Hurst, C. D., Platt, F. M. & Knowles, M. A. Comprehensive mutation analysis of the TERT promoter in bladder cancer and detection of mutations in voided urine. *Eur Urol* 65, 367-9 (2014).
28. Allory, Y. et al. Telomerase reverse transcriptase promoter mutations in bladder cancer: high frequency across stages, detection in urine, and lack of association with outcome. *Eur Urol* 65, 360-6 (2014).
29. Qu, Y. et al. Low frequency of TERT promoter mutations in a large cohort of gallbladder and gastric cancers. *Int J Cancer* 134, 2993-4 (2014).
30. Boisselier, B. et al. COLD PCR HRM: a highly sensitive detection method for IDH1 mutations. *Hum Mutat* 31, 1360-5 (2010).
31. Kinde, I. et al. TERT promoter mutations occur early in urothelial neoplasia and are biomarkers of early disease and disease recurrence in urine. *Cancer Res* 73, 7162-7 (2013).
32. Szankasi, P. et al. A quantitative allele-specific PCR test for the BRAF V600E mutation using a single heterozygous control plasmid for quantitation: a model for qPCR testing without standard curves. *J Mol Diagn* 15, 248-54 (2013).

We claim:

1. A method of testing a body sample of a human with a tumor, comprising:
   amplifying tumor DNA of a body sample of the human with a set of allele-specific amplification primers, wherein the set of allele-specific primers comprises sequences of SEQ ID NO: 2, 5, 8, and 12, wherein said allele-specific primers comprise an LNA-modified nucleotide at their 3' ends, wherein said amplifying further employs allele-non-specific amplification primers, wherein said allele-non-specific primers comprise sequences SEQ ID NO: 3, 6, 9, 10, 13, and 14 to generate amplification products comprising TERT promoter and IDH1 and IDH2 sequences when complementary templates are present in the body sample; and
   detecting the amplification products of said tumor DNA, wherein 0.1% mutant genomic DNA copies in a background of wild-type copies can be detected, and wherein 0.1% mutant genomic copies can be distinguished from 0% mutant genomic copies.

2. A method of testing a body sample of a human with a tumor, comprising:
   amplifying tumor DNA of a body sample of the human with a set of primers comprising the sequences of SEQ ID NO: 1-14, wherein the set comprises allele-specific amplification primers which comprise sequences of SEQ ID NO: 2, 5, 8, and 12, wherein said allele-specific primers comprise an LNA-modified nucleotide at their 3' ends, wherein said set further comprises allele-non-specific amplification primers which comprise sequences of SEQ ID NOS: 3, 6, 9, 10, 13, and 14, to generate amplification products comprising TERT promoter and IDH1 and IDH2 sequences when complementary templates are present in the body sample; and
   detecting the amplification products of said tumor DNA, wherein 0.1% mutant genomic DNA copies in a background of wild-type copies can be detected, and wherein 0.1% mutant genomic copies can be distinguished from 0% mutant genomic copies.

3. The method of claim 1 or 2 wherein the set of allele-specific amplification primers further comprises sequences of SEQ ID NO: 15-21.

4. The method of claim 3 wherein a tag sequence is attached to the 5' end of at least one of the primers.

5. The method of claim 1 or 2 wherein the tumor DNA is genomic DNA.

6. The method of claim 1 or 2 wherein the tumor DNA is genomic DNA that has been subjected to pre-amplification.

7. The method of claim 6 wherein the pre-amplification employs a DNA polymerase having a higher fidelity rate than Taq polymerase.

8. The method of claim 6 wherein the pre-amplification employs an annealing temperature of ≥66° C.

9. The method of claim 6 wherein the pre-amplification employs an annealing temperature of ≥68° C.

10. The method of claim 6 wherein the pre-amplification is conducted as a multiplex reaction.

11. The method of claim 1 or 2 wherein at least a portion of cycles of the amplifying are conducted at ≥66° C.

12. The method of claim 11 wherein a portion of the cycles of the amplifying are conducted at ≤60° C.

13. The method of claim 2 wherein separate aliquots of the tumor DNA of the body sample are amplified with sets of primers comprising (a) SEQ ID NO: 1-3; (b) SEQ ID NO: 4-6; (c) SEQ ID NO: 3 and 6; (d) SEQ ID NO: 7-9; (e) SEQ ID NO: 9 and 10; (f) SEQ ID NO: 11-13; and (g) SEQ ID NO: 13-14.

14. The method of claim 1 or 2 wherein the amplification is performed as a quantitative PCR.

15. The method of claim 1 or 2 wherein the body sample is selected from the group consisting of cerebral spinal fluid (CSF), blood, lymph, serum, plasma, urine, saliva, mucus, and tears.

16. The method of claim 1 or 2 wherein the body sample is a biopsy sample.

17. The method of claim 1 or 2 wherein the body sample is a needle aspirate.

18. The method of claim 1 or 2 wherein a tag sequence is attached to the 5' end of at least one of the primers.

19. The method of claim 1 wherein said set of allele-specific primers comprise primers each of which consist of a sequence selected from the group consisting of SEQ ID NO: 2, 5, 8 and 12.

20. The method of claim 1 wherein said set further comprises primers each of which consists of a sequence of SEQ ID NO: 1, 4, 7, and 11.

21. The method of claim 2 wherein said allele-specific primers comprise primers each of which consists of a sequence selected from the group consisting of SEQ ID NO: 1, 2, 4, 5, 7, 8, 11, and 12.

* * * * *